United States Patent
Korkuch (10) Patent No.: US 12,402,910 B2
(45) Date of Patent: Sep. 2, 2025

(54) MALLEABLE SHEATH BODY

(71) Applicant: ABIOMED, Inc., Danvers, MA (US)

(72) Inventor: Christopher Nason Korkuch, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 1214 days.

(21) Appl. No.: 17/034,350

(22) Filed: Sep. 28, 2020

(65) Prior Publication Data

US 2021/0093353 A1 Apr. 1, 2021

Related U.S. Application Data

(60) Provisional application No. 62/907,927, filed on Sep. 30, 2019.

(51) Int. Cl.
*A61B 17/34* (2006.01)
*A61L 29/06* (2006.01)
(Continued)

(52) U.S. Cl.
CPC .......... *A61B 17/3423* (2013.01); *A61L 29/06* (2013.01); *A61L 29/14* (2013.01);
(Continued)

(58) Field of Classification Search
CPC .. A61M 2025/0024; A61M 2025/0025; A61M 25/0023; A61M 25/0662; A61M 25/0026; A61B 17/3423; A61B 17/3415
See application file for complete search history.

(56) References Cited

U.S. PATENT DOCUMENTS 5,209,741 A 5/1993 Spaeth
5,674,240 A 10/1997 Bonutti et al.
(Continued)

FOREIGN PATENT DOCUMENTS

CN 101443067 A 5/2009
CN 102281914 A 12/2011
(Continued)

OTHER PUBLICATIONS

Office Action issued in Taiwanese Patent Application No. 109133887 on Dec. 19, 2023 (17 pp.).
(Continued)

*Primary Examiner* — Majid Jamialahmadi
(74) *Attorney, Agent, or Firm* — Botos Churchill IP Law LLP (57) ABSTRACT

A blood pump assembly includes an introducer sheath with a proximal end and a distal end, a pump body which extends within the introducer sheath, and a catheter that interfaces with the pump body and extends proximally though the introducer sheath. In a rest state, the introducer sheath forms an oval cross-section sized to encompass the catheter and a medical device. In a constrained state when the pump body is within the introducer sheath, the cross-section of the introducer sheath is circular. The malleability of the introducer sheath allows larger medical devices to be passed through the introducer sheath, while still allowing other devices to be inserted through the introducer sheath after the pump has been guided through. A perimeter of oval cross-section of the introducer sheath is equal to the perimeter of the circular cross-section of the introducer sheath.

18 Claims, 4 Drawing Sheets

(51) Int. Cl.
  *A61L 29/14* (2006.01)
  *A61M 25/00* (2006.01)
  *A61M 60/135* (2021.01)
  *A61B 17/00* (2006.01)
  *A61B 17/3207* (2006.01)
  *A61F 2/24* (2006.01)
  *A61F 2/95* (2013.01)
  *A61M 25/10* (2013.01)

(52) U.S. Cl.
  CPC . *A61M 60/135* (2021.01); *A61B 2017/00955* (2013.01); *A61B 17/3207* (2013.01); *A61B 17/3415* (2013.01); *A61F 2/2427* (2013.01); *A61F 2/95* (2013.01); *A61M 25/10* (2013.01)

(56) References Cited

U.S. PATENT DOCUMENTS

| | | | |
|---|---|---|---|
| 7,722,568 | B2 | 5/2010 | Lenker et al. |
| 2004/0167478 | A1 | 8/2004 | Mooney et al. |
| 2007/0021768 | A1 | 1/2007 | Nance et al. |
| 2010/0094259 | A1 | 4/2010 | Makower et al. |
| 2013/0211324 | A1 | 8/2013 | Voss et al. |
| 2014/0188216 | A1 | 7/2014 | Bishop et al. |
| 2014/0296769 | A1 | 10/2014 | Hyde et al. |
| 2016/0000499 | A1 | 1/2016 | Lennox et al. |
| 2016/0008588 | A1* | 1/2016 | Wada ............ A61M 25/0023 600/203 |
| 2019/0076167 | A1 | 3/2019 | Fantuzzi et al. |
| 2019/0307589 | A1* | 10/2019 | Goldberg ............ B29D 23/00 |

FOREIGN PATENT DOCUMENTS

| | | |
|---|---|---|
| CN | 102387830 A | 3/2012 |
| CN | 102727987 A | 10/2012 |
| CN | 105102011 A | 11/2015 |
| CN | 109862934 A | 6/2019 |
| EP | 2455128 B1 | 8/2015 |
| JP | 2006051406 A | 2/2006 |
| WO | 2011133486 A1 | 10/2011 |
| WO | 2014124283 A1 | 8/2014 |
| WO | 2014164009 A2 | 10/2014 |
| WO | 2017059186 A1 | 4/2017 |
| WO | 2019055591 A2 | 3/2019 |
| WO | 2019161245 A1 | 8/2019 |

OTHER PUBLICATIONS

The International Search Report and The Written Opinion for PCT/US2020/053035, Date of Mailing: Jan. 26, 2021.
CN First Office Action dated Nov. 17, 2023 for CN Appln. No. 202080077311.1.
Heckman, K., "Circle with the Same Perimeter as an Ellipse," available at https://www.vcalc.com/wiki/circle-ellipse-same-perimeter, (last visited Jun. 14, 2024)(6 pp.).
Office Action issued in Chinese Patent Application No. 2020800773111 on Aug. 29, 2024 (23 pp.).
Office Action issued in Japanese Patent Application No. 2022-520036 on Aug. 22, 2024 (9 pp.).
Office Action from Israeli Patent Application No. 291737 dated Jan. 6, 2025 (5 pp.).
Office Action issued in Chinese Patent Application No. 2020800773111 dated Jan. 26, 2025 (34 pp.).
Office Action issued in Indian Patent Application No. 202217021913 dated Mar. 5, 2025 (7 pp.).
Examination Report from Australian Patent Application No. 2020357500 dated Mar. 6, 2025 (4 pp.).
Office Action issued in European Patent Application No. 20789799.2 on Apr. 2, 2025 (7 pp.).
Office Action issued in Japanese Patent Application No. 2022-520036 dated Apr. 2, 2025 (4 pp.).
Office Action and Search Report issued in Taiwanese Patent Application No. 114101445 on Jul. 3, 2025 (7 pp.).

* cited by examiner

MALLEABLE SHEATH BODY

CROSS-REFERENCE TO RELATED APPLICATION

This application claims the benefit of priority from U.S. Provisional Application No. 62/907,927 filed Sep. 30, 2019, the contents of which are incorporated herein by reference.

BACKGROUND

Blood pumps are often used in combination with other medical devices for support and treatment of patients suffering from cardiovascular disease. Physicians may perform high risk percutaneous coronary interventions (HRPCI) while utilizing a blood pump to provide cardiac support during the procedure. Insertion of the blood pump and other devices needed for such a procedure typically requires two to three separate access locations into the arterial system. Each additional access location into the vasculature requires more time to prepare the access point, additional introducers, closers, and other devices, and may lead to complications at the surgical sites. Some patients suffering from cardiovascular disease may have only one available access point for arterial or venous access due to additional vascular issues. The lack of available access points can prevent physicians from gaining access to the vasculature and result in a reduced opportunity to treat the patient.

Some physicians attempt to address these issues by using a single access point to access the patient's vasculature and inserting multiple devices through a single introducer sheath, hub and valve placed at the access point. Using a single hub and introducer sheath to place multiple devices can complicate the ability to maintain the position of the first device during introduction and manipulation of the second, as well as poor hemostasis from the introduce valve. Larger devices may not be able to fit through the introducer sheath and valve, and after the larger device is placed smaller devices may not be able to fit through the introducer sheath alongside the catheter of the larger device. Attempting to introduce large or multiple devices through a single conventional introducer sheath may cause breakage of the introducer sheath and valve during insertion.

Because of such challenges, some physicians may choose not to use cardiovascular support devices like blood pumps when performing vascular intervention because of the difficulty in preparing multiple access sites to the vasculature. In such cases, a physician may proceed with the PCI, such as introduction of a stent, a balloon, a prosthetic valve, an additional catheter, a guide, or an atherectomy tool, and not provide simultaneous cardiac support with a blood pump. That decision may end up impairing the patient's ability to get the necessary mechanical circulatory support during the intervention.

Accordingly, there is a need for new technologies providing vascular access for multiple medical devices during cardiovascular interventions.

SUMMARY

The methods, systems, and devices described herein enable introduction of medical devices of varying sizes through a malleable introducer sheath. The malleability of the introducer sheath allows larger medical devices like pumps to be introduced through the introducer sheath, while still maintaining space for a catheter and other small devices to be inserted through the introducer sheath after the pump has been guided through.

In an aspect, a blood pump assembly includes an introducer sheath with a proximal end and a distal end, a pump body which extends within the introducer sheath, and a catheter which interfaces with the pump body and extending proximally through the introducer sheath. The introducer sheath forms an oval cross-section sized to encompass the catheter and a medical device.

In another aspect, an introducer sheath includes a proximal end with a first opening, a distal end with a second opening, and a sheath forming a lumen extending between the first openings and the second opening. For example, the sheath may be sized for insertion into an artery or vein of a patient. The first opening has a first cross-sectional shape in a rest state and a second cross-sectional shape in a constrained state. A circumference of the first cross-sectional shape is about the same as a circumference of the second cross-sectional shape. The first cross-sectional shape may be an oval, and the second cross-sectional shape may be a more circular shape. The oval cross-sectional shape of the first opening in the rest state allows multiple devices and catheters to be inserted through the introducer simultaneously, while the circular cross-sectional shape in the constrained state allows larger diameter devices to be inserted through the introducer sheath when necessary. In some implementations, the introducer sheath is malleable and passively forms a circular shape, or an irregular shape, when the larger diameter device is inserted through the lumen of the introducer sheath. For example, the introducer sheath may be sized so that a blood pump is able to pass through the lumen when the introducer sheath is in the constrained state having a circular cross-sectional shape, and a second medical device (such as a catheter, stent, or other device) may be passed through the lumen with the catheter of the blood pump while the introducer sheath is in the oval cross-sectioned rest state.

In another aspect, a method for introducing medical devices into vasculature of a patient by an introducer sheath that is configured to change shape so as to permit two or more different medical devices to pass through the sheath during insertion into the patient's vasculature. For example, the sheath may be sized and configured so that a blood pump may pass through the sheath lumen and be seated within a vessel of the patient, and also a stent, valve or other interventional device may also pass through the sheath lumen. Thereby, such multiple device assemblies may be positioned through a single sheath that is introduced in a single access site. In some implementations, the method involves inserting a distal end of an introducer sheath into a vessel of the patient, leaving the proximal end of the introducer sheath extending out from the vessel. The introducer sheath has a cross-section structured so as to permit passage of multiple medical devices therethrough. In some adaptations the sheath has a rest state and an expanded state. The sheath may be configured to take on an oval cross-sectional shape in a rest state, wherein the oval shape permits two medical devices (such as a pump and a stent, each via a delivery catheter) to pass simultaneously or in series through the sheath. The method may include introducing a first medical device into the proximal end of the introducer sheath (for example, the first medical device may include a distal medical device, such as a blood pump, and a proximal catheter), and guiding the first medical device (e.g., the blood pump) through the introducer sheath and out the distal end of the introducer sheath, such that the proximal catheter of the medical device extends through the introducer sheath and out of the proximal end of the introducer sheath. The method further includes introducing a second medical device (such as a stent, valve, or other device) into the proximal end of the introducer sheath (for example via a catheter) and guiding the second medical device through the introducer sheath, while the proximal catheter of the first medical device remains within the introducer sheath.

DETAILED DESCRIPTION

A malleable introducer sheath able to change between two or more cross-sectional shapes when devices are passed through the sheath allows larger medical devices like pumps to be introduced through the introducer sheath, while still maintaining space for a catheter and other smaller device to be inserted through the introducer sheath after the pump has been guided through.

By enabling the introduction of multiple devices through a single introducer sheath, only one access point into the patient's vasculature is required. Patients who have only one available arterial or vascular access point can receive both PCI and cardiac support through the same access point, thus improving medical outcomes. Additionally, a single access point requires only one sterile field and one closure which is less likely to produce complications.

Figure 1A:
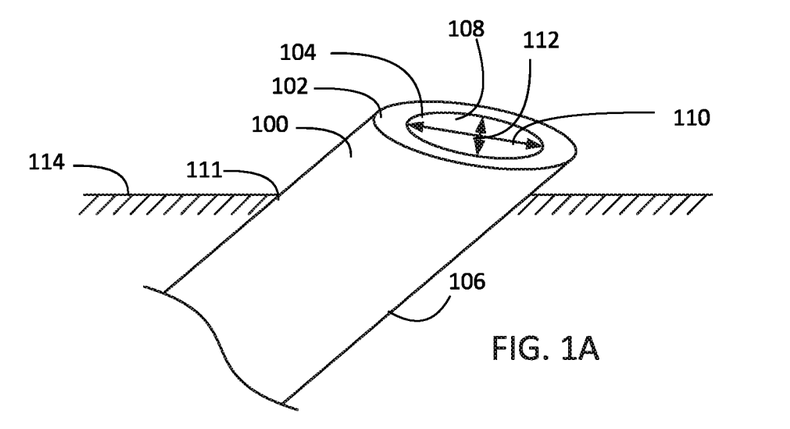
FIG. 1A shows a malleable introducer sheath in rest state.
Figure 1B:
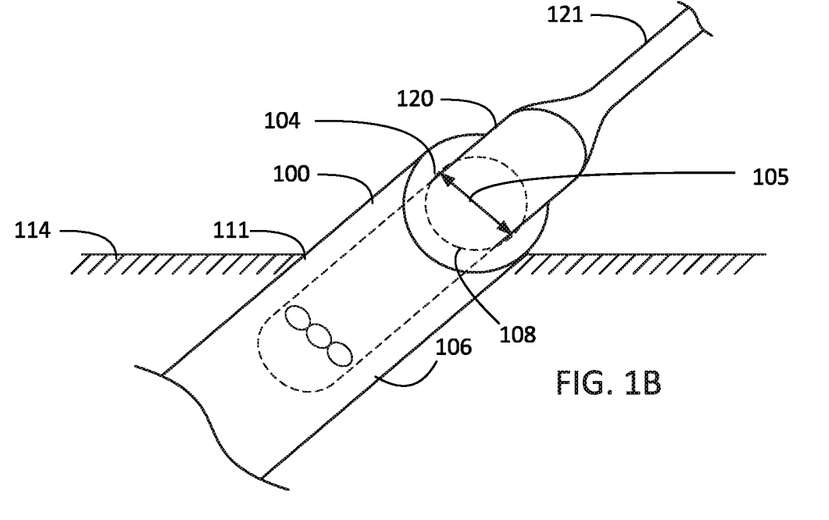
FIG. 1B shows the malleable introducer sheath in a constrained state during insertion of a medical device into the introducer sheath.
Figure 1C:
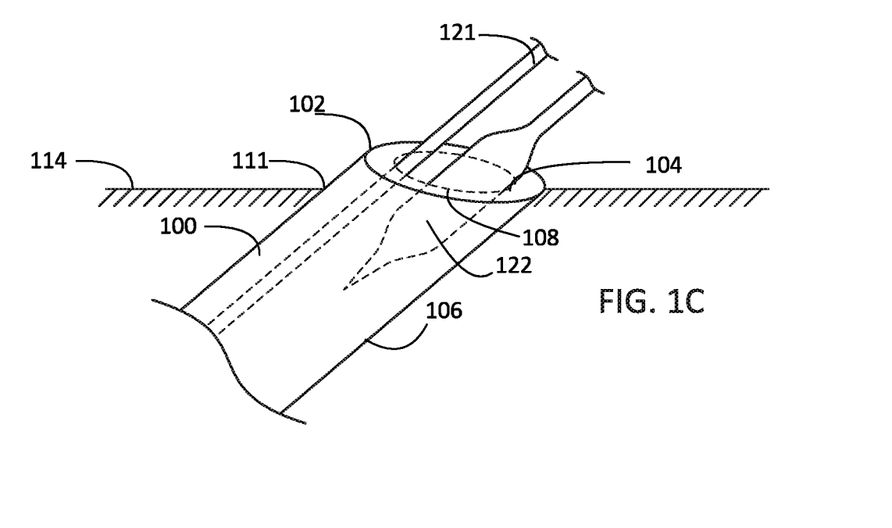
FIG. 1C shows the malleable introducer sheath in a rest state during insertion of second medical device into the introducer sheath.

FIGS. 1A-C illustrate the mechanism by which the malleable introducer sheath allows multiple devices to be inserted into the vasculature, showing the introducer sheath in a rest state before any devices are introduced (FIG. 1A), in a constrained state during insertion of a large medical device through the introducer sheath (FIG. 1B), and returned to the rest state after the large medical device has passed through the introducer sheath (FIG. 1C).

First, FIG. 1A shows the malleable introducer sheath 100 in a rest state. The introducer sheath 100 has a proximal end 102, a first opening 104, and a sheath 106 forming a lumen 108 extending through the sheath 106. The first opening has a width 110 and a height 112. The proximal end 102 of the introducer sheath 100 extends out of a vessel 114 of a patient at an incision 111. A distal end of the introducer sheath (not shown) extends within the vessel 114, and provides access to the vessel 114.

The first opening 104 has an oval cross-sectional shape in a rest state, such that the width 110 is greater than the height 112. The rest state of the introducer sheath 100 is unconstrained and is the shape to which the introducer sheath returns in the absence of forces acting on the sheath 106. The sheath 106 along the length of the introducer sheath 100 from the proximal end 102 to the distal end (not shown) has an oval cross-sectional shape. The sheath 106 has a smooth external surface, and a smooth internal surface within the lumen 108, to allow ease of introduction into the vessel 114 and to facilitate introduction of medical devices through the lumen 108 and into the vessel 114, respectively.

The introducer sheath 100 is formed from a material having an elastic modulus which allows flexibility and malleability of the material. As will be described in FIG. 2, the introducer sheath 100 has an oval cross-section in the rest state, but is capable of altering the cross-sectional shape to allow larger devices to be passed through the lumen 108. The introducer sheath 100 is formed from a material having an elastic modulus of 10 MPa to 1000 MPa, and may be formed from any of thermoplastic polyurethane, a polyether block amide plastic (PEBA), or a thermoplastic elastomer, or any other suitable material. In some implementations the introducer sheath is formed from a material having a target material stiffness between 70A and 40D hardness.

The oval cross-sectional shape of the introducer sheath 100 in the rest state may have a width 110 of 6.25 mm and a height 112 of 4 mm to 4.2 mm, or any other suitable dimensions. Ideally, the width 110 and height 112 of the introducer sheath 100 in the rest state is such that a 3 mm catheter and an 8 Fr sheath having a 10 Fr outer diameter are capable of fitting within the introducer sheath 100.

The incision 111 may be an arteriotomy incision oriented to be aligned in the circumferential direction of the vessel. The oval shape of the first opening 104 may be shaped to match the incision 111 in the vessel 114. An oval-shaped incision 111 may lead to improved results over a circular or other-shaped incision, because of the elastic properties of the vessel 114 which enable stretching of the vessel in certain directions. An oval-shaped incision 111 may also be easier to close following the completion of the procedure. Additionally, the oval-shaped cross-section of the introducer sheath allows introduction of additional or differently shaped devices than conventional introducer sheaths which are typically formed as perfectly round tubes which are most effective for the introduction of other round-shape devices.

The vessel of the patient may be accessed through the arteriotomy incision. In some embodiments, the size of the arteriotomy incision matches dimensions of the introducer sheath. In some embodiments, the vessel is a femoral artery. In some embodiments, the vessel is a radial artery.

The proximal end 102 of the introducer sheath 100 may be coupled to a hub (not shown). The hub may include one or more access points and one or more valves through which medical devices can be guided into the introducer sheath 100. In some implementations, the hub may provide a single access point which is coupled to the introducer sheath such that all medical devices to be inserted into the introducer sheath are guided through the same hub. In other implementations, the hub may include multiple access points for introduction of multiple medical devices into the vessel. Using the introducer sheath 100 with a hub designed to have multiple access points allows the individual manipulation and positioning of the medical devices in the vessels without concern about dislodging or moving them when they are introduced through the same valve or hub. Further, using the introducer sheath 100 with a hub designed to provide access to multiple devices improves patient safety because only one access point into the vessel is required and the hub, introducer sheath 100, and devices are unlikely to become damaged or break during introduction. An introducer sheath 100 designed to allow introduction of multiple devices through the sheath 106 can be used with a broader range of patients, including patients suffering from cardiovascular disease that limits the availability of vascular or arterial access points.

FIG. 1B shows the malleable introducer sheath 100 in a constrained state during insertion of a first medical device 120 into the introducer sheath 100. The introducer sheath 100 passively assumes a more circular shape when a first medical device 120 is passed through the lumen 108. The introducer sheath 100 has a diameter of about 5 mm in the constrained state. In some embodiments, the circular cross-section of the introducer sheath forms at an axial position along the introducer sheath that encapsulates a portion of the medical device.

In the constrained state, the width 110 and the height 112 of the introducer sheath 100 in the rest state are changed toward the radius 105 of the circular constrained state shown in FIG. 1B, although the introducer sheath 100 may not be truly circular. In FIG. 1B, the constrained state is illustrated as having a circular cross-section for convenience, but in some implementations the constrained state is oval in shape but with different dimensions than the rest state oval shape shown in FIG. 1A The introducer sheath 100 is passively manipulated into the constrained state by the passage of the first medical device 120 through the lumen 108, and the actual shape of the introducer sheath 100 lumen 108 and opening 104 is determined by the dimensions of the first medical device 120 passing through the lumen 108. When the introducer sheath 100 is truly circular in cross-section in a maximally constrained state, the radius 105 is about 5 mm such that a 5 mm circular medical device is capable of fitting within the introducer sheath. In some implementations, the radius 105 of the circular shape is 4 mm, 4.5 mm, 5 mm, 5.5 mm, 6 mm, 7 mm, or 8 mm. Ideally, the radius 105 of the introducer sheath 100 accommodates a first medical device of size 14 Fr.

In some implementations, the first medical device 120 may be a blood pump, an aortic valve replacement device, or an endovascular aneurysm repair device. For example, in FIG. 1B, the first medical device 120 is illustrated as a blood pump. The blood pump may have a cannula, impeller rotatably driven to pump blood, and a catheter 121 extending proximal of the cannula. The catheter may include electrical wires for controlling the blood pump. In some embodiments, the blood pump includes a rotor deployed inside a shroud and a motor coupled to the catheter. In some embodiments, the blood pump further comprises an introducer hub coupled to the proximal end of the introducer sheath. In some embodiments, the introducer hub comprises more than one introducer port. In some embodiments, the introducer hub comprises a valve.

FIG. 1C shows the malleable introducer sheath 100 in a rest state during insertion of a second medical device 122 into the introducer sheath 100. After the passage of the first medical device 120 (illustrated in FIG. 1B) through the introducer sheath 100, the introducer sheath 100 returns to the oval cross-sectional shape of the rest state. The catheter 121 of the first medical device 120 still extends through the introducer sheath 100, connecting the first medical device 120 to the proximal end 102 of the introducer sheath 100. The catheter 121 of the first medical device 120 has a smaller diameter than the first medical device 120 itself. The introducer sheath 100 is able to accommodate an additional second medical device 122 to be introduced into the vessel 114 through the introducer sheath 100 next to the catheter 121 of the first medical device 120 while the introducer sheath is in the rest state and has an oval cross-sectional shape.

In some embodiments, the cross-section of the introducer sheath 100 is configured to return from the circular cross-section to the oval cross-section when, e.g. the pump body of the first medical device 120 is distal of the distal end of the introducer sheath 100 and the catheter 121 extends from the pump body to the proximal end of the introducer sheath 100.

The introducer sheath 100 has the same perimeter of the opening 104 whether the introducer sheath 100 is in the rest state or the constrained state. The introducer sheath 100 has a smaller cross-sectional area in the oval rest state than in the constrained, more circular, state. The introducer sheath 100 in the rest state is statically oval, and changes cross-sectional shape temporarily to a more circular cross-sectional shape in order to accommodate the passage of the larger first medical device 120 through the lumen 108. The changeability in cross-sectional shape allows the introducer sheath 100 to accommodate devices that are bigger than statically round introducer sheaths may be able to, through a differently shaped sheath opening and sheath that has the same perimeter. For example, a sheath for use in PCI could be inserted through the introducer sheath 100 next to a 9 Fr catheter for a blood pump when the introducer sheath 100 is in the rest state, but these two medical devices could not fit through a conventional rigid introducer sheath together. A smaller cross-sectional area in the resting state is favorable for longer duration use of the introducer sheath 100 in the patient's body, because it takes up a smaller cross-section of the vessel, which provides more flow past the sheath, increasing distal perfusion.

While the hub is not shown in FIGS. 1A-1C for clarity, the sheath attachment to the hub can be circular or oval in shape. The minimum width of the oval, or diameter of the circular cross section, is ideally capable of accommodating a 3 mm diameter catheter and a 10 Fr sheath. In some implementations, the hub is rigid and not malleable, and must accommodate the devices through the hub without any change in the shape of the hub. The hub may have a larger cross-sectional area than the sheath in a resting state or a constrained state of the sheath. The sheath may have a circular or more-circular cross-section at the point of attachment to the hub, with a transition zone distal of the attachment, and a rest state of the sheath distal to the transition zone. In some implementations, the transition zone is less than 2 cm in length to avoid interaction with the arteriotomy.

Figure 2:
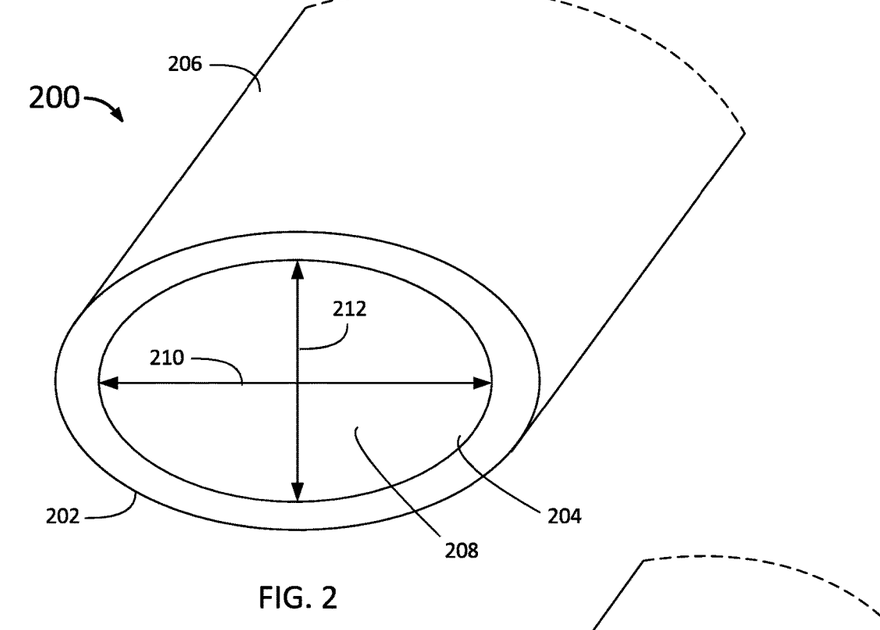
FIG. 2 shows a cross-section of a malleable introducer sheath in a rest state.

FIG. 2 shows a cross-section of a malleable introducer sheath 200 in a rest state. As described above with regard to FIGS. 1A and 1C, the introducer sheath 200 has an oval cross-sectional shape in the rest state. The introducer sheath 200 (for example introducer sheath 100 of FIGS. 1A-C) has a proximal end 202, a first opening 204, and a sheath 206 forming a lumen 208 extending through the sheath 206. The first opening 204 has a width 210 and a height 212.

In the rest state, the introducer sheath 200 is oval-shaped in cross-section at the first opening 204, and maintains the cross-sectional shape along a length of the sheath 206. The lumen 208 of the introducer sheath 200 is similarly oval-shaped in cross-section while in the rest state. The width 210 of the first opening 204 is greater than the height 212.

In some implementations, the first opening 204 has a width 210 of 6.25 mm and a height 212 of 4 mm to 4.2 mm, or any other suitable dimensions. Ideally, the width 210 and height 212 of the introducer sheath 200 first opening 204 in the rest state is such that a 3 mm catheter and an 8 Fr sheath having a 10 Fr outer diameter are capable of fitting within the introducer sheath 200.

In some implementations, the first opening 204 and a portion of the proximal end 202 of the sheath 206 are oval-shaped in cross-section while in the rest state, and a remainder of a length of the introducer sheath 200 is circular in shape or has a cross-sectional shape of a differently dimensioned oval. The sheath 206 is malleable, such that the introducer sheath 200 bends along the natural curves within the vasculature without kinking.

Figure 3:
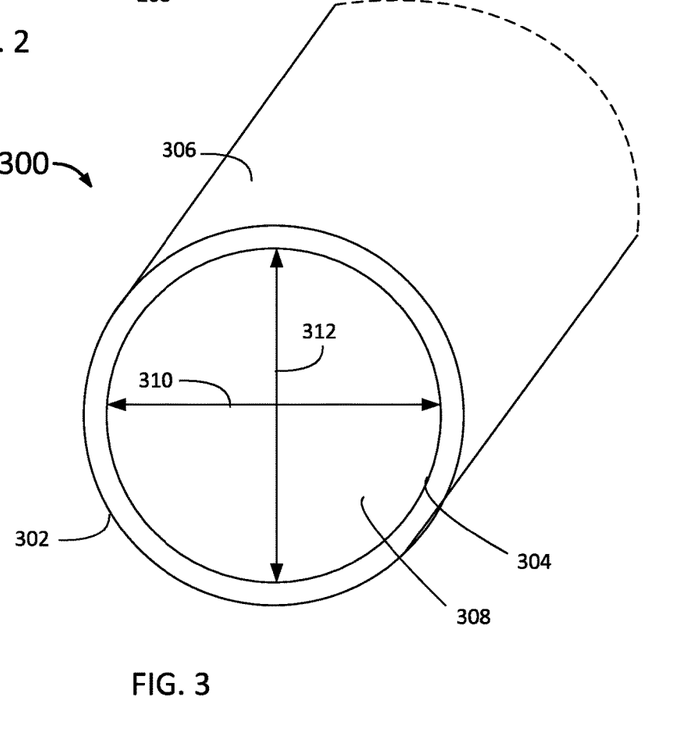
FIG. 3 shows a cross-section of a malleable introducer sheath in a constrained state.

FIG. 3 shows a cross-section of a malleable introducer sheath 300 in a constrained state. As described above with regard to FIG. 1B, the introducer sheath 300 has a circular cross-sectional shape in the constrained state, or a more circular cross-sectional shape than the cross-section of the introducer sheath in the rest state. The introducer sheath 300 (for example introducer sheath 100 of FIG. 1B) has a proximal end 302, a first opening 304, and a sheath 306 forming a lumen 308 extending through the sheath 306. The first opening has a width 310 and a height 312. While the width 310 and the height 312 are different from the width and height of the introducer sheath in the rest state (for example in FIG. 2), the perimeter of the first opening 304 is the same in both the rest and constrained states. The rest state configuration has a smaller cross-sectional area than in the constrained state.

In the constrained state, the introducer sheath 300 is circular in cross-sectional shape at the first opening 304 and along a length of the sheath 306. The introducer sheath 300 may be constrained by the passage of a medical device having a cross-section with a dimension larger than the width 310 or the height 312 of the introducer sheath 300 first opening 304, such that the first opening 304 changes in cross-sectional shape in order to accommodate the medical device. The malleable material of the introducer sheath 300 enables the introducer sheath to change in cross-sectional shape enough to allow the passage of the medical device through the lumen 308.

In some implementations, the introducer sheath 300 does not have a completely circular cross-sectional shape in the constrained state. Instead, the introducer sheath 300 may continue to be oval in cross-sectional shape, though the dimensions of the oval may be altered from the oval of the rest state. In some implementations, the introducer sheath 300 has a complex or irregular shape that mimics the shape of the device passing through the introducer sheath 300. In some implementations, the full length of the sheath 306 from the proximal end 302 to a distal end (not shown) has a consistent cross-sectional shape. In other implementations, only a portion of the introducer sheath 300 through which the medical device is currently passing has a circular or constrained cross-section.

In some implementations, the introducer sheath 300 is altered in its cross-sectional shape during the passage of one or more medical devices through the lumen 308. The medical device may be a blood pump, an aortic valve replacement device, or an endovascular aneurysm repair device. The introducer sheath 300 returns to the oval cross-sectional rest state after the medical device has been guided through the lumen 308 and into the vessel.

Figure 4:
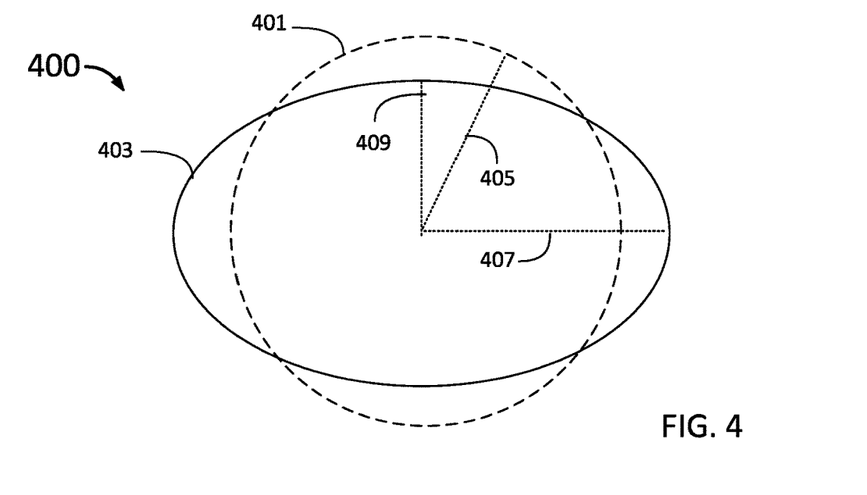
FIG. 4 shows a comparison of the cross-sectional shapes of an introducer sheath in a rest state and a constrained state.

FIG. 4 shows comparison of the cross-sectional shapes of an introducer sheath 400 in a rest state 403 and a constrained state 401. In the rest state 403, the introducer sheath 400 has a cross-section shaped as an oval, having a width 407 and a height 409. In the constrained state 401, the introducer sheath has a cross-section that is circular in shape, and has a radius 405.

In the rest state 403, the introducer sheath 400 has a width 407 of about 6.25 mm and a height 409 of about 4 mm. In some implementations, in the rest state the introducer sheath 400 has a width 407 of 5.25 mm, 5.5 mm, 5.75 mm, 6 mm, 6.25 mm, 6.5 mm, 6.75 mm, 7 mm, 7.25 mm, 7.5 mm, 8 mm, 9 mm, or any other suitable width. In some implementations, in the rest state the introducer sheath 400 has a height 412 of 3 mm, 3.5 mm, 3.75 mm, 4 mm, 4.25 mm, 4.5 mm, 4.75 mm, 5 mm, or any other suitable height. Ideally, the width 407 and height 409 of the introducer sheath 400 in the rest state is such that a 3 mm catheter and an 8 Fr sheath having a 10 Fr outer diameter are capable of fitting within the introducer sheath 400.

In the constrained state 401, the width 407 of the introducer sheath 400 decreases while the height 409 increases in order to accommodate the dimensions of a medical device being guided into and through the introducer sheath 400. The width 407 and the height 409 may approach the radius 405 of the circular shape in the constrained state. The radius 405 of the circular cross-sectional shape is about 5 mm. In some implementations, the radius of the circular cross-sectional shape is 4 mm, 4.5 mm, 5 mm, 5.5 mm, 6 mm, 7 mm, or 8 mm. The constrained state 401 may be circular, as shown in FIG. 4 for convenience, but in some implementations, the constrained state 401 is oval in shape, but with different dimensions than the rest state oval shape. In some implementations, the constrained state 401 is complex or irregular in cross-sectional shape, and the shape may mirror the shape and dimensions of the medical device being inserted through the introducer sheath 400. Ideally, the radius 405 of the introducer sheath 400 accommodates a medical device of size 14 Fr.

Figure 5:
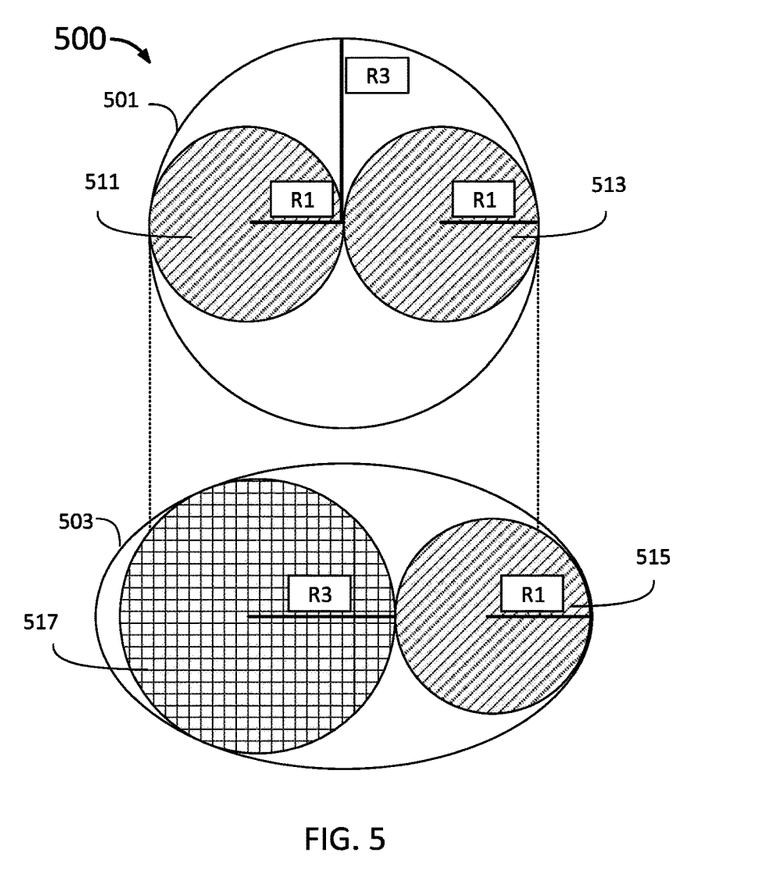
FIG. 5 shows a comparison of device sizes inserted into an introducer sheath in the rest state and the constrained state.

While the cross-sections of the introducer sheath 400 opening in the rest state 403 and the constrained state 401 are constant, the size of medical devices which are able to pass through the opening vary depending on the dimensions of the opening. FIG. 5 shows a comparison of the device sizes that can be inserted into an introducer sheath 500 in the rest state 503 (for example rest state 403 in FIG. 4) and the constrained state 501 (for example constrained state 401 in FIG. 4).

The introducer sheath 500 in the constrained state 501 is circular in cross-sectional shape, or more circular in cross-sectional shape than in the rest state, and is able to pass larger medical devices through the lumen. The lumen of the introducer sheath 500 in the constrained state 501 is sized so as to be able to accommodate, for example, two devices (511 and 513) of radius R1, or one larger device of radius R3. The introducer sheath 500 in the rest state 503 is oval in cross-sectional shape. The longer width of the oval shape enables the introducer sheath 500 in the rest state 503 to accommodate multiple devices of varying sized, for example, the introducer sheath 500 in the rest state 503 is able to accommodate a first device 515 of radius R1, and a second device 517 of larger radius R3. The cross-sectional area of the lumen in the rest state 503 is smaller than the cross-sectional area in the constrained state 501.

The variation in cross-sectional shape of the introducer sheath 500 when a larger device (such as device of radius R3) is passed through the introducer sheath 500 is possible due to the malleability of the introducer sheath. In the rest state 503, when multiple medical devices are being inserted through the introducer sheath 500, larger bore medical devices are able to be guided through the introducer sheath 500 lumen (for example second medical device 517) while other medical devices (for example first medical device 515) extend through the introducer sheath lumen.

In an example, the introducer sheath 500 may assume the circular cross-section constrained state 501 as a blood pump is inserted into the vessel through the introducer sheath 500 lumen. The circular cross-sectional shape of the constrained state 501 accommodates the large diameter of the blood pump as it passes through the introducer sheath 500. For example, the blood pump may have radius R3. Once the blood pump has passed through the introducer sheath 500, and the catheter remains within the introducer sheath 500 lumen (for example as first medical device 515), and the introducer sheath 500 returns to the rest state 503. A second medical device 517 may then be passed through the introducer sheath 500 in the rest state 503 alongside the catheter (first medical device 515). The second medical device may be a balloon, a stent, a prosthetic valve, a second catheter, a guide, or an atherectomy tool. The second medical device 517 would not fit through a conventional rigid introducer sheath alongside the catheter (first medical device 515). The ability of the introducer sheath to change in cross-sectional shape to accommodate medical devices being guided through the lumen, the introducer sheath is more versatile and provides a mechanism for physicians to safely gain access to a patient's vasculature for cardiovascular interventions.

While the rest state is described herein as having an oval cross-sectional shape, while the constrained state is described as a more circular cross-sectional shaped sheath, it is considered that the rest state could have a circular cross-section allowing passage of large bore medical devices, and a constrained state of the introducer sheath could be oval in shape to accommodate multiple devices of smaller diameter and dimensions.

In some embodiments, a therapy is provided with the first medical device within the vasculature of the patient. In some embodiments, an electrical signal is provided to the first medical device through the proximal catheter of the first medical device. In some embodiments, a therapy is provided with the second medical device within the vasculature of the patient.

Figure 6:
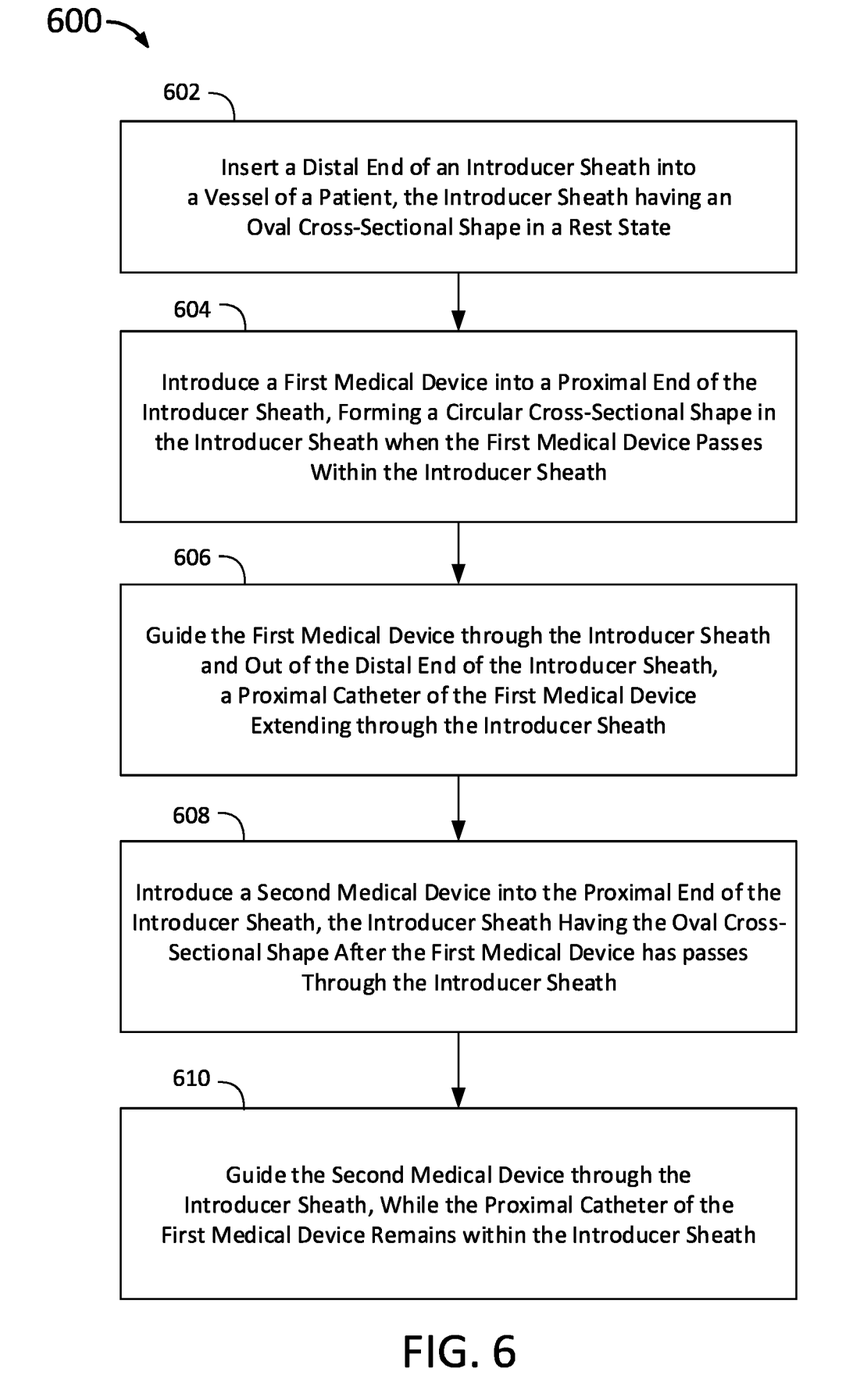
FIG. 6 shows a flow chart illustrating a method for introducing medical devices into vasculature of a patient using a malleable introducer sheath.

FIG. 6 shows a flow chart 600 illustrating a method for introducing medical devices into vasculature of a patient using a malleable introducer sheath. In step 602, a distal end of an introducer sheath (for example introducer sheath 100 in FIGS. 1A-C, introducer sheath 200 in FIG. 2, introducer sheath 300 in FIG. 3, introducer sheath 400 in FIG. 4, or introducer sheath 500 in FIG. 5) is inserted into a vessel of a patient. The introducer sheath has an oval cross-sectional shape in the rest state, such that when there are no forces acting on the introducer sheath, the introducer sheath is oval in cross-section along the length of the introducer sheath from the proximal end to the distal end. In some implementations, the introducer sheath is oval is cross-sectional shape only at a proximal end of the introducer sheath, or over some portion of the introducer sheath.

In step 604, a first medical device is introduced into a proximal end of the introducer sheath, forming a circular cross-sectional shape in the introducer sheath when the first medical device passes within the introducer sheath. The introducer sheath is formed as a malleable sheath that passively takes on a circular shape when a medical device is introduced to the introducer sheath which is larger than a dimension, such as width or height, of the introducer sheath opening in the rest state. The introducer sheath opening has the same perimeter in the oval rest state as in the constrained circular state, but the dimensions are altered to allow passage of the medical device through the introducer sheath. The introducer sheath opening has a smaller cross-sectional area in the rest state as compared to the constrained state. At step 606, the first medical device is guided through the introducer sheath and out of the distal end of the introducer sheath. The first medical device has a catheter extending proximally from a body of the first medical device, and the proximal catheter extends through the introducer sheath from the distal end of the introducer sheath to the proximal end of the introducer sheath. The first medical device may be a blood pump, an aortic valve replacement device, or an endovascular aneurysm repair device.

At step 608, a second medical device is introduced into the proximal end of the introducer sheath, the introducer sheath having returned to the oval cross-sectional shape in the rest state after the passage of the first medical device through the introducer sheath. The second medical device may be a balloon, a stent, a prosthetic valve, a second catheter, a guide, or an atherectomy tool. The introducer sheath is sized in the rest state to accommodate the second medical device as well as the proximal catheter of the first medical device. At step 610, the second medical device is guided through the introducer sheath while the proximal catheter of the first medical device remains within the introducer sheath.

A malleable introducer sheath passively able to be changed in cross-sectional shape from an oval rest state to a more circular or fully circular cross-sectional shape when a larger medical device is passed through the lumen of the sheath allows the passage of multiple medical devices through a single introducer sheath, decreasing the need for multiple access points. The malleable cross-sectional shape of the introducer sheath further allows passage of larger medical devices, while still maintaining a rest state cross-sectional shape that provides a better shape for an arteriotomy and through which multiple smaller devices can extend during a cardiovascular procedure.

Using a malleable introducer sheath capable of changing in cross-sectional shape with a hub that has multiple access points for introducing multiple medical devices allows a physician to insert the devices through a single access point in the vessel and to maintain the relative positions of the devices during introduction and manipulation of the other devices, promoting patient safety and efficient treatment of the patient.

In some embodiments, a second arteriotomy incision is made in a second vessel, and a sheath, catheter, or medical device is inserted through the second arteriotomy incision.

The foregoing is merely illustrative of the principles of the disclosure, and the apparatuses can be practiced by other than the described aspects, which are presented for purposes of illustration and not of limitation. It is to be understood that the apparatuses disclosed herein, while shown for use in percutaneous insertion of heart pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

ILLUSTRATIVE EMBODIMENTS

Embodiment A

A1: A blood pump assembly comprising:
an introducer sheath having a proximal end and a distal end;
a pump body configured to extend within the introducer sheath;
a catheter configured to interface with the pump body and extend proximally through the introducer sheath;
wherein the introducer sheath forms an oval cross-section that is sized to encompass the catheter and a medical device.

A2: The blood pump assembly of A1, wherein the pump body includes a rotor deployed inside a shroud, a motor, and wherein the motor is coupled to the catheter.

A3: The blood pump assembly of any of A1-A2, wherein the cross-section of the introducer sheath is configured to be circular when the pump body is within the introducer sheath.

A4: The blood pump assembly of any of A1-A3, wherein the cross-section of the introducer sheath is configured to return from the circular cross-section to the oval cross-section when the pump body is distal of the distal end of the introducer sheath and the catheter extends from the pump body to the proximal end of the introducer sheath.

A5: The blood pump assembly of any of A3-A4, wherein the introducer sheath has the oval cross-section in a free state.

A6: The blood pump assembly of any of A2-A5, wherein the introducer sheath has the circular cross-section in a constrained state.

A7: The blood pump assembly of any of A2-A6, wherein a perimeter of the introducer sheath is configured to be constant between the oval cross-section and the circular cross-section.

A8: The blood pump assembly of any of A2-A7, wherein the oval cross-section of the introducer sheath has a first cross-sectional area, and the circular cross-section of the introducer sheath has a second cross-sectional area, the second cross-sectional area being larger than the first cross-sectional area.

A9: The blood pump assembly of A8, wherein the first cross-sectional area of the oval cross-section of the introducer sheath is configured to accommodate a 3 mm catheter and an 8 Fr sheath.

A10: The blood pump assembly of any of A7-A9, wherein the oval cross-section of the introducer sheath has a height of about 4 mm and a width of about 6.25 mm.

A11: The blood pump assembly of any of A7-A10, wherein the height and the width of the oval cross-section of the introducer sheath depends on a size of the medical device.

A12: The blood pump assembly of any of A7-A11, wherein the height and the width of the oval cross-section of the introducer sheath are configured to match a size of an arteriotomy.

A13: The blood pump assembly of any of A7-A12, wherein the height and width of the oval cross-section of the introducer sheath are constant from the proximal end to the distal end of the introducer sheath.

A14: The blood pump assembly of any of A1-A13, wherein the introducer sheath is a 14 Fr introducer sheath.

A15: The blood pump assembly of any of A2-A14, wherein the circular cross-section of the introducer sheath has a diameter of 5 mm.

A16: The blood pump assembly of any of A2-A15, wherein the circular cross-section of the introducer sheath has a constant diameter from the proximal end to the distal end of the sheath.

A17: The blood pump assembly of any of A1-A16, wherein an external surface of the introducer sheath is configured to be smooth from the proximal end to the distal end of the introducer sheath.

A18: The blood pump assembly of any of A1-A17, wherein the introducer sheath is configured to have a material stiffness of 70A-40D.

A19: The blood pump assembly of any of A1-A18, wherein the introducer sheath is configured to have an elastic modulus between 10 MPa and 1000 MPa.

A20: The blood pump assembly of any of A1-A9, wherein the introducer sheath comprises one of a thermoplastic polyurethane, a polyether block amide plastic (PEBA), or a thermoplastic elastomer.

A21: The blood pump assembly of any of A1-A20, further comprising an introducer hub coupled to the proximal end of the introducer sheath.

A22: The blood pump assembly of A21, wherein the introducer hub comprises more than one introducer port.

A23: The blood pump assembly of A21 or A22, wherein the introducer hub comprises a valve.

A24: The blood pump assembly of any of A1-A23, wherein the medical device is a balloon, a stent, a prosthetic valve, a second catheter, a guide, or an atherectomy tool.

Embodiment B

B1: An introducer sheath, comprising:
a proximal end having a first opening;
a distal end having a second opening;
a sheath forming a lumen extending between the first opening and the second opening;
wherein the first opening is configured to have a first cross-sectional shape in a rest state and a second cross-sectional shape in a constrained state, and
wherein a circumference of the first cross-sectional shape is the same as a circumference of the second cross-sectional shape.

B2: The introducer sheath of B1, wherein the first cross-sectional shape is an oval.

B3: The introducer sheath of B1 or B2, wherein the second cross-sectional shape is a circle.

B4: The introducer sheath of any of B1-B3, wherein the first opening is configured to have the second cross-sectional shape when a device is passed through the first opening into the lumen.

B5: The introducer sheath of B4, wherein the first opening is configured to return from the second cross-sectional shape to the first cross-sectional shape after the device is passed through the lumen.

B6: The introducer sheath of B5, wherein a height and a width of the first opening in the first cross-sectional shape depend on a size of the device.

B7: The introducer sheath of B6, wherein the height and the width of the first opening in the first cross-sectional shape are configured to accommodate a 3 mm catheter and an 8 Fr sheath.

B8: The introducer sheath of B7, wherein a height of the first opening in the first cross-sectional shape is about 4 mm, and a width of the first opening in the first cross-sectional shape is about 6.25 mm.

B9: The introducer sheath of any of B1-B8, wherein a cross-sectional area of the first opening in the first cross-sectional shape is configured to be smaller than a cross-sectional area of the first opening in the second cross-sectional shape.

B10: The introducer sheath of B1-B8, wherein a height and a width of the first opening in the first cross-sectional shape are configured to match a size of an arteriotomy.

B11: The introducer sheath of B1-B10, wherein dimensions of the first opening in the first cross-sectional shape are constant along a length of the sheath.

B12: The introducer sheath of any of B1-B11, wherein a perimeter of the first opening is configured to be constant between the first cross-sectional shape and the second cross-sectional shape.

B13: The introducer sheath of any of B1-B12, wherein the first opening has an inner diameter of about 5 mm in the second cross-sectional shape.

B14: The introducer sheath of B13, wherein the lumen is configured to have an internal diameter equal to the inner diameter of the first opening in the second cross-sectional shape.

B15: The introducer sheath of any of B1-B14, wherein the sheath is configured to have an outer diameter of 14 Fr when the first opening is in the second cross-sectional shape.

B16: The introducer sheath of any of B1-B15, wherein an external surface of the sheath is configured to be smooth from the proximal end to the distal end.

B17: The introducer sheath of any of B1-B16, wherein the sheath is configured to have a material stiffness of 70A-40D.

B18: The introducer sheath of any of B1-B17, wherein the sheath is configured to have an elastic modulus between 10 MPa and 1000 MPa.

B19: The introducer sheath of any of B1-B18, wherein the sheath comprises one of a thermoplastic polyurethane, a polyether block amide plastic (PEBA), or a thermoplastic elastomer.

B20: The introducer sheath of any of B1-B19, wherein the proximal end is configured to be coupled to an introducer hub.

B21: The introducer sheath of any of B1-B20, wherein the device is one of a balloon, a stent, a prosthetic valve, a second catheter, a guide, or an atherectomy tool.

Embodiment C

C1: A method for introducing a medical device into vasculature of a patient, the method comprising:
inserting a distal end of an introducer sheath into a vessel of the patient, a proximal end of the introducer sheath extending out from the vessel, the introducer sheath having an oval cross-sectional shape in a rest state;
introducing a first medical device into the proximal end of the introducer sheath, the first medical device comprising a distal medical device and a proximal catheter;
guiding the first medical device through the introducer sheath and out the distal end of the introducer sheath, such that the proximal catheter of the medical device extends through the introducer sheath and out of the proximal end of the introducer sheath;
introducing a second medical device into the proximal end of the introducer sheath; and
guiding the second medical device through the introducer sheath, while the proximal catheter of the first medical device remains within the introducer sheath.

C2: The method of C1, wherein introducing the first medical device forms a circular cross-sectional shape in the introducer sheath when the first medical device passes within the introducer sheath.

C3: The method of C2, wherein the circular cross-section forms within the introducer sheath at an axial position along the introducer sheath that encapsulates a portion of the medical device.

C4: The method of C2 or C3, wherein the circular cross-sectional shape formed within the introducer sheath has a circumference equal to a circumference of the oval cross-sectional shape of the introducer sheath in the rest state.

C5: The method of any of C2-C4, wherein the circular cross-sectional shape formed within the introducer sheath has a cross-sectional area larger than a cross-sectional area of the oval cross-sectional shape of the introducer sheath in the rest state.

C6: The method of any of C2-C5, wherein the circular cross-section forms within the introducer sheath along a length of the introducer sheath from the proximal end to the distal end.

C7: The method of any of C2-C6, wherein after the first medical device has been guided out of the distal end of the introducer sheath, the introducer sheath forms the oval cross-sectional shape.

C8: The method of any of C1-C7, wherein the first medical device is a blood pump.

C9: The method of C8, wherein the blood pump includes a rotor deployed inside a shroud, and a motor coupled to the proximal catheter.

C10: The method of any of C1-C9, wherein the second medical device is a balloon, a stent, a prosthetic valve, a second catheter, a guide, or an atherectomy tool.

C11: The method of any of C1-C10, further comprising:
providing a therapy with the first medical device within the vasculature of the patient.

C12: The method of any of C1-C11, further comprising:
providing an electrical signal to the first medical device through the proximal catheter of the first medical device.

C13: The method of any of C1-C12, further comprising:
providing a therapy with the second medical device within the vasculature of the patient.

C14: The method of any of C1-C13, further comprising:
making an arteriotomy incision in the vessel, a size of the arteriotomy matching dimensions of the introducer sheath; and
accessing the vessel of the patient through the arteriotomy incision.

C15: The method of C14, wherein making an arteriotomy incision in the vessel, a size of the arteriotomy matching dimensions of the introducer sheath further comprises:
making an arteriotomy incision in a femoral artery.

C16: The method of C14, wherein making an arteriotomy incision in the vessel, a size of the arteriotomy matching dimensions of the introducer sheath further comprises:
making an arteriotomy incision in a radial artery.

C17: The method of C14, further comprising:
making a second arteriotomy incision in a second vessel; and
introducing a sheath, catheter, or medical device through the second arteriotomy.

What is claimed is:

1. A system, comprising:
   a medical device; and
   an introducer sheath comprising a proximal end, a distal end, and
   an introducer sheath body forming a lumen extending between a first opening at the proximal end and a second opening at the distal end,
   wherein the first opening is configured to have a first cross-sectional shape in a rest state and a second cross-sectional shape in a constrained state,
   wherein the first cross-sectional shape is an oval and the second cross-sectional shape is a circle,
   wherein the first opening is configured to have the second cross-sectional shape when the medical device is passed through the first opening into the lumen, and
   wherein a circumference of the first cross-sectional shape is the same as a circumference of the second cross-sectional shape.

2. The system of claim 1, wherein the first opening is configured to return from the second cross-sectional shape to the first cross-sectional shape after the medical device is passed through the lumen.

3. The system of claim 2, wherein a height and a width of the first opening in the first cross-sectional shape depend on a size of the medical device.

4. The system of claim 3, wherein the height and the width of the first opening in the first cross-sectional shape are configured to accommodate a 3 mm catheter and an 8 Fr sheath.

5. The system of claim 4, wherein the height of the first opening in the first cross-sectional shape is about 4 mm, and the width of the first opening in the first cross-sectional shape is about 6.25 mm.

6. The system of claim 1, wherein a cross-sectional area of the first opening in the first cross-sectional shape is configured to be smaller than a cross-sectional area of the first opening in the second cross-sectional shape.

7. The system of claim 1, wherein a height and a width of the first opening in the first cross-sectional shape are configured to match a size of an arteriotomy.

8. The system of claim 1, wherein dimensions of the first opening in the first cross-sectional shape are constant along a length of the introducer sheath.

9. The system of claim 1, wherein a perimeter of the first opening is configured to be constant between the first cross-sectional shape and the second cross-sectional shape.

10. The system of claim 1, wherein the first opening has an inner diameter of about 5 mm in the second cross-sectional shape.

11. The system of claim 1, wherein the lumen is configured to have an internal diameter equal to an inner diameter of the first opening in the second cross-sectional shape.

12. The system of claim 1, wherein the introducer sheath is configured to have an outer diameter of 14 Fr when the first opening is in the second cross-sectional shape.

13. The system of claim 1, wherein an external surface of the introducer sheath is configured to be smooth from the proximal end to the distal end.

14. The system of claim 1, wherein the introducer sheath is configured to have a material stiffness of 70A-40D.

15. The system of claim 1, wherein the introducer sheath is configured to have an elastic modulus between 10 MPa and 1000 MPa.

16. The system of claim 1, wherein the introducer sheath comprises one of a thermoplastic polyurethane, a polyether block amide plastic (PEBA), or a thermoplastic elastomer.

17. The system introducer sheath of claim 1, wherein the proximal end is configured to be coupled to an introducer hub.

18. The system of claim 1, wherein the medical device is one of a balloon, a stent, a prosthetic valve, a second catheter, a guide, or an atherectomy tool.

* * * * *

UNITED STATES PATENT AND TRADEMARK OFFICE
CERTIFICATE OF CORRECTION

| | | |
|---|---|---|
| PATENT NO. | : 12,402,910 B2 | Page 1 of 1 |
| APPLICATION NO. | : 17/034350 | |
| DATED | : September 2, 2025 | |
| INVENTOR(S) | : Christopher Nason Korkuch | |

It is certified that error appears in the above-identified patent and that said Letters Patent is hereby corrected as shown below:

In the Specification

Detailed Description
Column 8, Line 10:
Now reads: "412"; should read -- 409 --

Detailed Description
Column 11, Line 55:
Now reads: "All:"; should read -- A11: --

In the Claims

Claim 17
Column 16, Line 31:
Now reads: "system introducer sheath"; should read -- system --

Signed and Sealed this
Eighteenth Day of November, 2025

John A. Squires
*Director of the United States Patent and Trademark Office*